(12) United States Patent
Scherlitz-Hofmann et al.

(10) Patent No.: US 8,026,229 B2
(45) Date of Patent: Sep. 27, 2011

(54) ANTITUMOR-ACTIVE 2-ALKOXYESTRADIOL SULFAMATES

(75) Inventors: Ina Scherlitz-Hofmann, Falkensee (DE); Jens Hoffmann, Mühlenbeck (DE); Alexander Hillisch, Jena (DE); Eberhard Unger, Cospeda (DE); Tobias Neumann, Jena (DE); Sigfrid Schwarz, Jena (DE); Olaf Peters, Jena (DE); Thomas Michel, Leipzig (DE)

(73) Assignee: Sterix Limited, Berkshire (GB)

( * ) Notice: Subject to any disclaimer, the term of this patent is extended or adjusted under 35 U.S.C. 154(b) by 579 days.

(21) Appl. No.: 10/217,165

(22) Filed: Aug. 13, 2002

(65) Prior Publication Data

US 2003/0100544 A1    May 29, 2003

Related U.S. Application Data

(60) Provisional application No. 60/382,974, filed on May 23, 2002.

(30) Foreign Application Priority Data

Aug. 13, 2001 (DE) .................................. 101 39 494

(51) Int. Cl.
*A61K 31/56* (2006.01)
*C07J 1/00* (2006.01)
(52) U.S. Cl. ........ 514/178; 514/180; 514/182; 552/623; 552/626; 552/627; 552/635
(58) Field of Classification Search .............. 552/611, 552/522, 531, 540, 543, 544, 556, 558, 652, 552/626, 650, 623, 627, 635; 514/176, 178, 514/182, 841, 843, 179, 180
See application file for complete search history.

(56) References Cited

U.S. PATENT DOCUMENTS

| | | | |
|---|---|---|---|
| 5,705,495 A * | 1/1998 | Schwarz et al. | 514/182 |
| 5,830,886 A | 11/1998 | Reed et al. | |
| 5,880,115 A * | 3/1999 | Li et al. | 514/169 |
| 6,011,024 A | 1/2000 | Reed et al. | |
| 6,046,186 A | 4/2000 | Tanabe et al. | |
| 6,136,992 A | 10/2000 | Ram et al. | |
| 6,339,079 B1 | 1/2002 | Kasch et al. | |
| 6,376,687 B1 * | 4/2002 | Li et al. | 552/611 |
| 6,399,595 B1 * | 6/2002 | Li et al. | 514/182 |
| 6,436,917 B1 * | 8/2002 | Droescher et al. | 514/176 |
| 6,436,918 B1 * | 8/2002 | Li et al. | 514/182 |
| 6,569,844 B1 * | 5/2003 | Schwarz et al. | 514/176 |
| 6,583,130 B1 * | 6/2003 | Schwarz et al. | 514/176 |
| 6,841,548 B2 * | 1/2005 | Schwarz et al. | 514/178 |
| 7,078,395 B1 | 7/2006 | Reed et al. | |
| 7,119,081 B2 | 10/2006 | Potter et al. | |
| 2003/0100544 A1 | 5/2003 | Scherlitz-Hofmann et al. | |
| 2004/0014781 A1 | 1/2004 | Elger et al. | |
| 2004/0254241 A1 | 12/2004 | Ino et al. | |
| 2006/0122161 A1 | 6/2006 | Reed et al. | |
| 2006/0281719 A1 | 12/2006 | Lloyd Potter et al. | |

FOREIGN PATENT DOCUMENTS

| | | |
|---|---|---|
| DE | 4239945 A1 | 6/1994 |
| DE | 4239946 A1 | 6/1994 |
| EP | 12 944 02 | 3/2003 |
| WO | WO 93/05064 A1 | 3/1993 |
| WO | WO 96/05216 A1 | 2/1996 |
| WO | WO 96/05217 A1 | 2/1996 |
| WO | WO 97/14712 A2 | 4/1997 |
| WO | WO 98/24802 A2 | 6/1998 |
| WO | WO 98/40398 A1 | 9/1998 |
| WO | WO 98/42729 A2 | 10/1998 |
| WO | WO 99/33858 A2 | 7/1999 |
| WO | WO 00/06175 A1 | 2/2000 |

(Continued)

OTHER PUBLICATIONS

Draetta et al "Section V. Topics in Biology", Annual Reports in Medicinal Chemistry, 31, 1996, Academic Press, San Diego, pp. 241-246.*

(Continued)

*Primary Examiner* — Sabiha Qazi
(74) *Attorney, Agent, or Firm* — Hunton & Williams LLP (57) ABSTRACT

The present invention relates to the use of 2-alkoxyestrogen sulfamates of general formula I

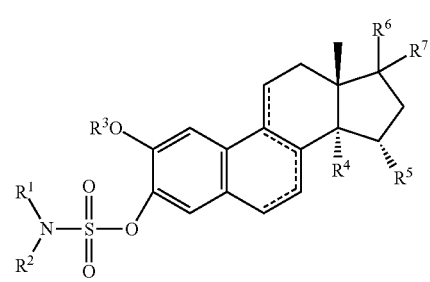

wherein
$R^1$ and $R^2$ independently represent H, methyl, $C_1$-$C_4$ acyl, benzoyl
$R^3$ represents $C_1$-$C_4$ alkyl or a group of formula $C_nF_mH_o$, wherein n=1, 2, 3, 4, 5 or 6, m>1, and m+o=2n+1,
$R^4$ and $R^5$ in each case represent H or, together, a methylene group or an additional double bond,
$R^6$ represents H,
$R^7$ represents OH, $OC_1$-$C_4$-alkyl, $OC_1$-$C_{11}$-acyl or $OSO_2NR^1R^2$,
the dashed lines in the B and C rings of the steroid skeleton additionally representing up to two double bonds,
for the production of a medical drug for the treatment of tumor diseases which can be affected positively by inhibiting the tubulin polymerization.
The inventive compounds are distinguished by the 2-alkoxy substitution in conjunction with the 17-hydroxy substitution. They have a special effect with regard to inhibiting tubulin polymerization and can be used, for example, for the treatment of prostate cancers.

21 Claims, 2 Drawing Sheets

FOREIGN PATENT DOCUMENTS

| WO | WO 00/06695 | 2/2000 |
|---|---|---|
| WO | WO 00/08374 | 2/2000 |
| WO | WO 00/66095 | 11/2000 |
| WO | WO 00/76487 A2 | 12/2000 |
| WO | WO 01/18028 A1 | 3/2001 |
| WO | WO 01/91797 | 12/2001 |
| WO | WO 02/16392 | 2/2002 |
| WO | WO 03/015792 | 2/2003 |
| WO | WO 03/020690 | 3/2003 |
| WO | WO 03/100544 | 12/2003 |
| WO | WO 2004/014781 | 2/2004 |
| WO | WO 2004/025241 | 3/2004 |

OTHER PUBLICATIONS

Joseph R. Bertino and Sydney E. Salmon "Principles of Cancer Therapy", Oncology XIV, pp. 1060-1074, 21st Edition, vol. 1 (2000), Edited by Lee Goldman, M.D. and J. Claude Bennett, M.D.*

Balasubramanian et al "Recent Developments in Cancer, Etc." Annual Reports in Medicinal Chemistry, 33, 1998, Academic Press, San Diego, pp. 151-159.*

Hazeldine et al "Design, Synthesis, and Biological Evaluation of Analogues of the Antitumor Agent," AN 2001:301100 HCAPLUS, DN 135:76849, Journal of Medicinal Chemistry, (2001), 44(11), 1758-1776.*

Beak et al., "The Tertiary Amide as an Effective Director of Ortho Lithiation," *J. Org. Chem.* 1982, 47, 34-46.

Culig et al., "Switch from antagonist to agonist of the androgen receptor blocker bicalutamide is associated with prostate tumour progression in a new model system," *British Journal of Cancer* (1999), 81(2), pp. 242-251.

Cushman et al., "Synthesis of Analogs of 2-Methoxyestradiol with Enhanced Inhibitory Effects on Tubulin Polymerization and Cancer Cell Growth," *J. Med. Chem.* 1997, 40, 2323-2334.

Cushman et al., "Synthesis, Antitubulin and Antimitotic Activity, and Cytotoxicity of Analogs of 2-Methoxyestradiol, an Endogenous Mammalian Metabolite of Estradiol That Inhibits Tubulin Polymerization by Binding to the Colchicine Binding Site," *J. Med. Chem.* 1995, 38, 2041-2049.

Fotsis et al., "The endogenous oestrogen metabolite 2-methoxyoestradiol inhibits and angiogenesis and suppresses tumour growth," *Nature* 1994, 368, 237-239.

Lin et al., "Comparison of 2-Methoxyestradiol-Induced, Docetaxel-Induced, and Paclitaxel-Induced Apoptosis in Hepatoma Cells and its Correlation with Reactive Oxygen Species," *Cancer* 2000, 89(5), 983-994.

Lowry et al., "Protein Measurement with the Folin Phenol Reagent," *Journ. Biol. Chem.* 1951, 193, 265-275.

Morrogh et al., "Differential Effects of Estrone and Estrone-3-O-Sulfamate Derivatives on Mitotic Arrest, Apoptosis, and Microtubule Assembly in Human Breast Cancer Cells," *Cancer Research* 2000, 60, 5441-5450.

Nambara et al., "Studies on Steroid Conjugates. III. New Syntheses of 2-Methoxyestrogens," *Chem. Phar. Bull.* 1970, 18(3), 474-480.

Pert et al., "Formylation of Oestrogens," *Aust. J. Chem.* 1989, 42, 405-419.

Prousa et al., "Synthese, Reaktivität und $^1$H-NMR-Daten von 14,15-Methylenderivaten der Androstan- und Östratrienreihe," *Journal f. prakt. Chem.* 1986, 328, 55-70.

Purohit et al., "The Effect of 2-Methoxyoestrone-3-O-Sulphamate on the Growth of Breast Cancer Cells and Induced Mammary Tumours," *Int. J. Cancer* 2000, 85, 584-589.

Purohit et al., "Recent advances in the development of steroid sulphatase inhibitors," *Journal of Steroid Biochemistry and Molecular Biology* 1999, 69, 227-238.

Schwarz et al., "Synthesis of estrogen sulfamates: Compounds with a novel endocrinological profile," *Steroids* 1996, 61, 710-717.

Shelanski et al., "Microtubule Assembly in the Absence of Added Nucleotides," *Proc. Nat. Acad. Sci.* 1973, 70(3), 765-768.

Siemann et al., "A novel synthesis of 14α, 15α-methylene estradiol (J 824)," *Steroids* 1995, 60, 308-315.

Singh et al., "Inhibition of deoxyglucose uptake in MCF-7 breast cancer cells by 2-methoxyestrone and 2-methoxyestrone-3-O-sulfamate," *Molecular and Cellular Endocrinology* 2000, 160, 61-66.

Snieckus, "Directed Ortho Metalation. Tertiary Amide and O-Carbamate Directors in Synthetic Strategies for Polysubstituted Aromatics," *Chemical Reviews* 1990, 90, 879-933.

Steenbrugge et al., "Biological Effects of Hormonal Treatment Regimens on a Transplantable Human Prostatic Tumor Line (PC-82)," *The Journal of Urology* 1984, 131, 812-817.

Wiley & Sons, "The E1 Mechanism," *Eliminations* 1985, Chapter 17, pp. 990-991.

Wiley & Sons, "Protection for Phenols," *Protection for Phenols and Catechols* 1999, pp. 249-276.

Elger, "Sulfamates of Various Estrogens are Prodrugs with Increased Systematic and Reduced Hepatic Estrogenicity at Oral Application", Journal of Steroid Biochemistry and Molecular Biology, vol. 55, No. 3-4, pp. 395-403, (1995).

Purohit, et al., "The Development of A-Ring Modified Analogues of Oestrone-3-O-Sulphamate as Potent Steroid Sulphatase Inhibitors with Reduced Oestrogenicity", Journal of Steroid Biochemistry and Molecular Biology, vol. 64, No. 5-6, pp. 269-275, (1998).

Purohit, et al., "Non-Steroidal and Steroidal Sulfamates: New Drugs for Cancer Therapy", Molecular and Cellular Endocrinology, vol. 171, pp. 129-135, (2001).

Index from Remington's Pharmaceutical Science, 16$^{th}$ Edition, Mack Publishing Company (1980).

* cited by examiner

FIGURE 1

Inhibition of the growth of a hormone-dependent, xenotransplanted prostate carcinoma (PC82) by treatment with substance A in comparison with castration and the casodex anti-androgen

FIGURE 2

ANTITUMOR-ACTIVE 2-ALKOXYESTRADIOL SULFAMATES

The present invention relates to 2-alkoxyestradiol sulfamates and their use in producing pharmaceuticals which have antitumor-effective activity.

Microtubuli are organelles, which occur in most eukaryotic cells and take on a number of functions therein, such as mitosis, intracellular movement and cell migration and define the shape of cells. Microtubuli are polymers of tubulin which, in turn, is a dimer of an α and a β unit. These heterodimers bind two molecules of guanosine triphosphate (GTP), one of the GTPs being bound permanently and the other exchangeably. The heterodimers polymerize in a head-to-tail arrangement into filamentous macromolecules, the so-called protofilaments, which, in turn, assemble to form tubular organelles, the microtubuli. Microtubuli are synthesized and disintegrated constantly. The equilibrium between growth and disintegration depends on the availability of new GTP tubulin subunits and on the rate of hydrolysis of the second bound GTP. At the plus end, new subunits are added and of the minus end, subunits diffuse away. It is known that cytotoxic substances, such as colchicine, vinblastine, vincristine, taxol, epothilone, podophyllotoxin, steganicin, combretastatin and methoxyestradiol affect the synthesis and disintegration of the microtubuli (tubulin polymerization and depolymerization) and, accordingly, are capable of affecting cell division in a phase-specific manner. This is the case especially for rapidly growing, neoplastic cells, the growth of which is largely unaffected by intracellular control mechanisms. In principle, active substances of this type are suitable for the treatment of malignant tumors. Fotsis et al., Nature 1994, 368, 237-239, report that 2-methoxyestradiol inhibits tumor growth and angiogenesis.

Cushman et al., J. Med. Chem. 1995, 38, 2041-2049, have investigated the cytotoxic effect, as well as the tubulin polymerization-inhibiting effect of 2-methoxyestradiol, and have reported in J. Med. Chem. 1997, 40, 2323-2334, that 2-alkoxy-6-oximinoestradiol derivatives inhibit tubulin polymerization and binding of [$^3$H]-colchicine to tubulin. With respect to the inhibition of tubulin polymerization, the 2-alkoxy-6-oximinoestradiol derivatives mentioned herein show an activity comparable to that of 2-ethoxyestradiol, the activity of which is higher than that of 2-methoxyestradiol.

In an effort to increase the oral bioavailability of 2-alkoxyestradiol, especially of 2-methoxyestradiol, the 3-hydroxy function of selected 2-alkoxyestradiol derivatives was subjected to sulfamoylation according to the present invention. In doing so, it was determined that the resulting 2-alkoxyestradiol sulfamates not only have improved bioavailability, but also inhibit the polymerization of tubulin more strongly compared to the 2-alkoxyestradiols themselves. Consequently, the corresponding sulfamates of the invention also have in vivo anti-tumor activity.

Specifically with estradiol and closely related derivatives, it has been well-known that introduction of a sulfamate group results in increased bioavailability in vivo (Elger et al., J. Steroid Biochem. and Mol. Biol. 1995, 55, 395). The improved bioavailability results from the binding of these substances to erythrocytes, in which they metabolize more slowly and are released successively. On the other hand, estrogens which have not been sulfamoylated, are subject upon oral administration to a very rapid hepatic metabolization (first pass effect). Schwarz et al., Steroids 1996, 61, 710-717, have described the synthesis of estrogen sulfamates.

On the other hand, steroid-3-sulfamates have been described as inhibitors of steroid sulfatase.

WO 93/05064 relates, among other things, to compounds of formula wherein each $R^1$ and $R^2$ independently represents hydrogen or a methyl group, with the proviso that at least one of the $R^1$ and $R^2$ residues is a hydrogen atom and the residue O-polycycle is a 3-sterol, the sulfate ester of which can be hydrolyzed by an enzyme with steroid sulfatase activity. Compounds substituted specifically in the 2 position of the steroid skeleton have not been disclosed explicitly.

U.S. Pat. No. 6,011,024 is based on WO 93/05064 and covers, for example, all compounds, in which the primary sulfamate function is linked to a 6-membered ring. Once again, compounds specifically substituted in the 2 position of the steroid skeleton have not been, disclosed explicitly.

WO 96/05216 relates to C2-unsubstituted estra-1,3,5(10)-triene sulfamate derivatives.

WO 96/05217 relates to pharmaceutical compositions which include active substances of general formula wherein R=$NH_2$, $R^3$=$C_{1-5}$ alkoxy group, OH; $R^8$, $R^9$ and $R^{10}$ independently=H or OH; $R^9$ and $R^{10}$ together may represent O. The pharmaceutical compositions disclosed therein can be used for female fertility control, menopausal HRT and for the treatment of gynecological or andrological syndromes, such as breast cancer or prostate cancer.

WO 97/14712 relates to steroid sulfamate derivatives of general formula wherein $R^1$ may represent an acyl, alkoxycarbonyl, aminocarbonyl, sulfonyl or sulfonamidyl group; $R^2$ may represent a hydrogen or a metal atom; $R^7$ and $R^8$ independently may represent H, OH and $C_{1-5}$ alkoxy; $R^{13}$, $R^{12}$, $R^{11}$ independently may represent H or OH.

WO 98/42729 relates to 16-halo-substituted 1,3,5-estratriene monosulfamates and to 3,17β-bissulfamates which may be alkoxy-substituted at C2. The 16-halogen substitution increases the sulfatase inhibition effect as well as the estrogenicity of the corresponding sulfamate derivatives.

The introduction of a 17-sulfamate function, in addition to the 3-sulfamate function, decreases the estrogenicity dramatically.

WO 98/24802 relates to sulfamates which inhibit estrone sulfatase. 2-Methoxyestrone sulfamate is named explicitly. In the specification, breast cancer, but not prostate cancer, is named as a potential area of therapy. Similarly, WO 99/33858 describes estrone sulfatase inhibitors of formula wherein $R^1$ and $R^2$ independently represent H, alkyl or, together, piperidine, morpholine or piperazine; $R^3$ H, CN, $NO_2$, $CO_2R^4$; $R^8$=H, $NO_2$ or $NR^6R^7$. In the specification, breast cancer is mentioned as a possible area of therapy.

WO 99/64013 relates to a pharmaceutical composition of a sulfamate derivative with a cell signal modifier (such as TNFα). In this combination, 2-methoxyestrone sulfamate is claimed explicitly as a preferred sulfamate; however, numerous other steroid 3-sulfamates also fall within the scope of the general formula. What is described as the mechanism of action of the inventive pharmaceutical compositions or of the steroid 3-sulfamates contained therein (preferably with at least one 2-alkoxy substituent) is 1) inhibition of glucose absorption in tumor cells, 2) inhibition of tumor angiogenesis, 3) disintegration of the micro tubuli, 4) induction of apoptosis. WO 00/76487 relates to materials which inhibit the TNFα-induced aromatase activity. As such, 2-alkoxyestrone 3-sulfamates, preferably 2-methoxyestrone sulfamate, have been claimed.

WO 01/18028 relates to non-estrogenic, estrone sulfatase-inhibiting N-acyl-18a-substituted steroid 3-sulfamates such as 16α-fluoro-2-methoxy-18a-homoestradiol N-acetylsulfamate or 16α-fluoro-2-methoxy-18a-homoestrone N-acetyl-sulfamate.

In Cancer 2000, 85, 983-994, the 2-methoxyestradiol-, docetaxel- and paclitaxelinduced apoptoses in hepatoma cells and their correlation with reactive oxygen species are compared.

Potter et al., Int. J. Cancer 2000, 85, 584-589, have investigated the effect of 2-methoxyestrone sulfamate in comparison with that of 2-methoxyestrone on the growth of breast cancer cells and induced breast tumors and found 2-methoxyestrone sulfamate has an appreciable therapeutic potential for the treatment of breast cancer.

Potter et al., Molecular and Cellular Endocrinology 2000, 160, 61-66, have investigated the inhibition of the absorption of desoxyglucose in MCF-7 breast cancer cells by 2-methoxyestrone and 2-methoxyestrone 3-sulfamate, which inhibit the absorption of glucose by 25 to 49% at 10 μM (likewise 2-methoxyestradiol and 2-methoxyestrone), and conclude that the compounds, because of their ability to inhibit the absorption of glucose, have therapeutic potential for inhibiting breast cancer.

Potter et al., Cancer Research 2000, 60, 5441-5450, have described 2-methoxyestrone sulfamate and 2-ethoxyestrone sulfamate as new antimicrotubuli-active compounds which have in vitro anti-cancer activity in breast carcinoma cells and therefore can possibly also be active in vivo. J. Steroid Biochem. and Mol. Biol. 1999, 69, 227-238, reports that the inhibition of steroid sulfatase activity is an important starting point for the treatment of hormonedependent breast cancers. 2-Methoxyestrone sulfamate, 17-deoxyestrone sulfamate and estrone sulfamate are mentioned explicitly. While monocyclic or bicyclic non-steroidal sulfamates inhibit steroid sulfatase, they are not as effective as the corresponding steroid derivatives.

It is the object of the present invention to provide compounds which inhibit tubulin polymerization more effectively than does 2-methoxyestradiol and, at the same time have a higher oral bioavailability.

According to the invention, said object is accomplished by the compounds of general formula I used in the production of a medical drug for the treatment of tumor diseases responding favorably to inhibition of the tubulin polymerization:

wherein
$R^1$ and $R^2$ independently represent H, methyl, $C_1$-$C_4$ acyl, benzoyl $R^3$ represents $C_1$-$C_4$ alkyl or a group of formula $C_nF_mH_o$, wherein n=1, 2, 3, 4, 5 or 6, m>1, and m+o=2n+1, $R^4$ and $R^5$ in each case represent H or, together, a methylene group or an additional bond, $R^6$ represents H, $R^7$ represents OH, $OC_1$-$C_4$-alkyl, $OC_1$-$C_{11}$-acyl or $OSO_2NR^1R^2$, the dashed lines in the B and C rings of the steroid skeleton additionally representing up to two double bonds.

Surprisingly, the 2-alkoxyestradiol sulfamates of the invention were found to have a stronger in vitro inhibiting effect on tubulin polymerization than 2-methoxyestradiol itself. The compounds of the invention also have in vivo anti-tumor activity.

As a result of the improved inhibition of tubulin polymerization, a stronger inhibition of tumor growth can be expected.

If $R^3$ represents a $C_1$-$C_4$ alkyl group, it may be a methyl, ethyl, n-propyl, isopropyl or n-, iso- or t-butyl group. A methyl or ethyl group is preferred.

In the event that $R^1$ and $R^2$ represents an acyl group, it may be a formyl, acetyl, propionyl, butyryl or isobutyryl group.

For the partially or fully fluorinated alkyl group in the $R^3$ substituent, a trifluoromethyl, pentafluoroethyl or 2,2,2-trifluoroethyl group is possible, for example.

The R⁷ alkoxy group may represent a methoxy, ethoxy, n-propoxy, isopropoxy, or n-, iso- or t-butoxy group.

An R⁷ acyloxy group is e.g. an acetyloxy, propionyloxy, butyryloxy, isobutyryloxy, valeryloxy, decyloxy, or undecyloxy group.

According to the present invention, those compounds of general formula I are preferred wherein:

$R^1$ represents H, methyl, acetyl, propionyl, butyryl,
$R^2$ represents H,
$R^3$ represents $C_1$-$C_4$ alkyl or $CH_2CF_3$,
$R^4$ and $R^5$ represent H or, together, a methylene group,
$R^6$ represents H,
$R^7$ represents OH, $OC_1$-$C_4$-alkyl, $OC_1$-$C_{11}$-acyl or $OSO_2NR^1R^2$, the broken line in the B and C rings of the steroid structure may additionally represent an 8-double bond.

According to the invention, the compounds listed below and the use thereof are particularly preferred:

1) 2-methoxy-17β-hydroxy-estra-1,3,5(10)-trien-3-yl sulfamate
2) 2-methoxy-17α-hydroxy-estra-1,3,5(10)-trien-3-yl sulfamate
3) 2-methoxy-17β-hydroxy-estra-1,3,5(10)-trien-3-yl N-acetylsulfamate
4) 2-methoxy-17α-hydroxy-estra-1,3,5(10)-trien-3-yl N-acetylsulfamate
5) 2-methoxy-17β-hydroxy-14α,15α-methylene-estra-1,3,5(10)-trien-3-yl sulfamate
6) 2-methoxy-17α-hydroxy-14α,15α-methylene-estra-1,3,5(10)-trien-3-yl sulfamate
7) 2-methoxy-17β-hydroxy-14α,15α-methylene-estra-1,3,5(10)-trien-3-yl N-acetylsulfamate
8) 2-methoxy-17α-hydroxy-14α,15α-methylene-estra-1,3,5(10)-trien-3-yl N-acetylsulfamate
9) 2-methoxy-17β-hydroxy-14α,15α-methylene-estra-1,3,5(10),8-tetraen-3-yl sulfamate
10) 2-methoxy-17α-hydroxy-14α,15β-methylene-estra-1,3,5(10),8-tetraen-3-yl sulfamate
11) 2-methoxy-17β-hydroxy-14α,15α-methylene-estra-1,3,5(10),8-tetraen-3-yl N-acetylsulfamate
12) 2-methoxy-17α-hydroxy-14α,15α-methylene-estra-1,3,5(10),8-tetraen-3-yl N-acetylsulfamate
13) 2-ethoxy-17β-hydroxy-estra-1,3,5(10)-trien-3-yl sulfamate
14) 2-ethoxy-17α-hydroxy-estra-1,3,5(10)-trien-3-yl sulfamate
15) 2-ethoxy-17β-hydroxy-estra-1,3,5(10)-trien-3-yl N-acetylsulfamate
16) 2-ethoxy-17α-hydroxy-estra-1,3,5(10)-trien-3-yl N-acetylsulfamate
17) 2-ethoxy-17β-hydroxy-14α,15α-methylene-estra-1,3,5(10)-trien-3-yl sulfamate
18) 2-ethoxy-17α-hydroxy-14α,15α-methylene-estra-1,3,5(10)-trien-3-yl sulfamate
19) 2-ethoxy-17β-hydroxy-14α,15α-methylene-estra-1,3,5(10)-trien-3-yl N-acetylsulfamate
20) 2-ethoxy-17α-hydroxy-14α,15α-methylene-estra-1,3,5(10)-trien-3-yl N-acetylsulfamate
21) 2-ethoxy-17β-hydroxy-14α,15α-methylene-estra-1,3,5(10),8-tetraen-3-yl sulfamate
22) 2-ethoxy-17α-hydroxy-14α,15α-methylene-estra-1,3,5(10),8-tetraen-3-yl sulfamate
23) 2-ethoxy-17β-hydroxy-14α,15α-methylene-estra-1,3,5(10),8-tetraen-3-yl acetylsulfamate
24) 2-ethoxy-17α-hydroxy-14α,15α-methylene-estra-1,3,5(10),8-tetraen-3-yl acetylsulfamate
25) 2-(2',2',2'-trifluoroethoxy)-17β-hydroxy-estra-1,3,5(10)-trien-3-yl sulfamate
26) 2-(2',2',2'-trifluoroethoxy)-17α-hydroxy-estra-1,3,5(10)-trien-3-yl sulfamate
27) 2-(2',2',2'-trifluoroethoxy)-17β-hydroxy-estra-1,3,5(10)-trien-3-yl N-acetylsulfamate
2-(2',2',2'-trifluoroethoxy)-17α-hydroxy-estra-1,3,5(10)-trien-3-yl N-acetylsulfamate
29) 2-(2',2',2'-trifluoroethoxy)-17β-hydroxy-14α,15α-methylene-estra-1,3,5(10)-trien-3-yl sulfamate
30) 2-(2',2',2'-trifluoroethoxy)-17α-hydroxy-14α,15α-methylene-estra-1,3,5(10)-trien-3-yl sulfamate
31) 2-(2',2',2'-trifluoroethoxy)-17β-hydroxy-14α,15α-methylene-estra-1,3,5(10),8-tetraen-3-yl sulfamate
32) 2-(2',2',2'-trifluoroethoxy)-17α-hydroxy-14α,15α-methylene-estra-1,3,5(10),8-tetraen-3-yl sulfamate
33) 2-(2',2',2'-trifluoroethoxy)-17β-hydroxy-14α,15α-methylene-estra-1,3,5(10)-trien-3-yl N-acetylsulfamate
34) 2-(2',2',2'-trifluoroethoxy)-17α-hydroxy-14α,15α-methylene-estra-1,3,5(10)-trien-3-yl N-acetylsulfamate
35) 2-(2',2',2'-trifluoroethoxy)-17β-hydroxy-14α,15α-methylene-estra-1,3,5(10),8-tetraen-3-yl N-acetylsulfamate
36) 2-(2',2',2'-trifluoroethoxy)-17α-hydroxy-14α,15α-methylene-estra-5(10),8-tetraen-3-yl N-acetylsulfamate Pharmacological Data The inventive compounds were tested in various models. The inventive compounds of general formula I are remarkable in that they inhibit tubulin polymerization more than does 2-methoxyestradiol. The effect on tubulin polymerization was tested in vitro in the following way:

Microtubular protein was purified by the method of Shelanski et al. (Shelanski et al., Proc. Natl. Acad. Sci. USA 1973, 70, 765-8) via cyclic assembly/disassembly from porcine brains. The buffer system used had the following composition: 20 mM PIPES (1,4-piperazinediethanesulfonic acid, pKa 6.8), 80 mM NaCl, 0.5 mM $MgCl_2$, 1 mM EGTA (ethylene glycol bis(2-aminoethyl)tetraacetic acid). Protein concentrations of 1 mg/ml (approx. $10^{-5}$ mM tubulin) were used to test the active substance. The protein was determined by the method of Lowry (Lowry et al., J. Biol. Chem. 1951, 193, 265-75) using bovine serum albumin as standard. The assembly of the microtubuli was carried out in the presence of 0.25 mM GTP and heating of the samples to 37° C.

Microtubulus formation was checked using turbidimetry at a wavelength of 340 nm. The state of equilibrium, at which the microtubular protein shows no increase in the concentration of assemblate (corresponding to the concentration of microtubuli) and turbidity no longer increases, is typically reached after 20 minutes.

The active substances were tested by adding them at the beginning of the assembly or at the state of equilibrium. Their effectiveness is characterized by deviations in the turbidity curves from those of the control. To check the effect and evaluate the turbidity values measured, a transmission electron microscopic examination (CEM 902 A, Zeiss, Oberkochen, Germany) of the assemblate was always carried out after negative staining with 1% aqueous uranyl acetate.

TABLE 1

| Name | Structure | Inhibition of tubulin polymerization $IC_{50}$ [µM] |
|---|---|---|
| 2-Methoxyestradiol | | >3 |
| 2-Methoxyestrone-3-sulfamate | | 1.6 |
| 2-Methoxy-17β-estradiol-3-sulfamate | | 1.0 |

The following abbreviations were used in the figures listed herein:

| | |
|---|---|
| Casodex: | N-[4'-cyano-3-(trifluorophenyl)]-3-[(4-fluorophenyl)sulfonyl]-2-hydroxy-2-methylpropanamide |
| A: | 2-methoxy-17β-estradiol 3-sulfamate (Example 1); |
| B: | 2-methoxy-17β-estradiol 3-(N-acetylsulfamate) (Example 6). |

In the present invention, the effect of the inventive 2-alkoxyestradiol sulfamates on tumor growth was investigated in vivo by means of mouse xenograft models, the inventive compounds being administered continuously on the subcutaneous route.

The PC82 tumor model (G. Steenbrugge, University of Rotterdam, The Netherlands Literature Steenbrugge et al., J. Urology 131:812-817, 1984) is a hormonedependent human prostate cancer model. The tumor model was established on immune-deficient nude mice by serial passaging of prostate carcinoma tissue removed during surgery and propagated further. The androgen-dependent LNCaP prostate carcinoma model was also established from a patient tumor. This tumor model grows both in cell culture and as a xenotransplant on immune-deficient mice (Culig, Hoffmann, But J. Cancer, 1999, 242-251). For the therapy experiments, 6-week old, male, nude mice (NMRI mice, M&B Bomholdtgard, Denmark) are supplemented with testosterone pellets (12.5 mg, 90-day release; IRA, Sarasota, Fla.). Either LNCaP cells ($1.5 \times 10^6$ cells) or small PC82 tumor fragments (2×2 mm) were implanted in, the animals (subcutaneously into the left side). After the tumors had reached a size of 20-25 mm², treatment with the inventive substances was commenced.

Figure 1:
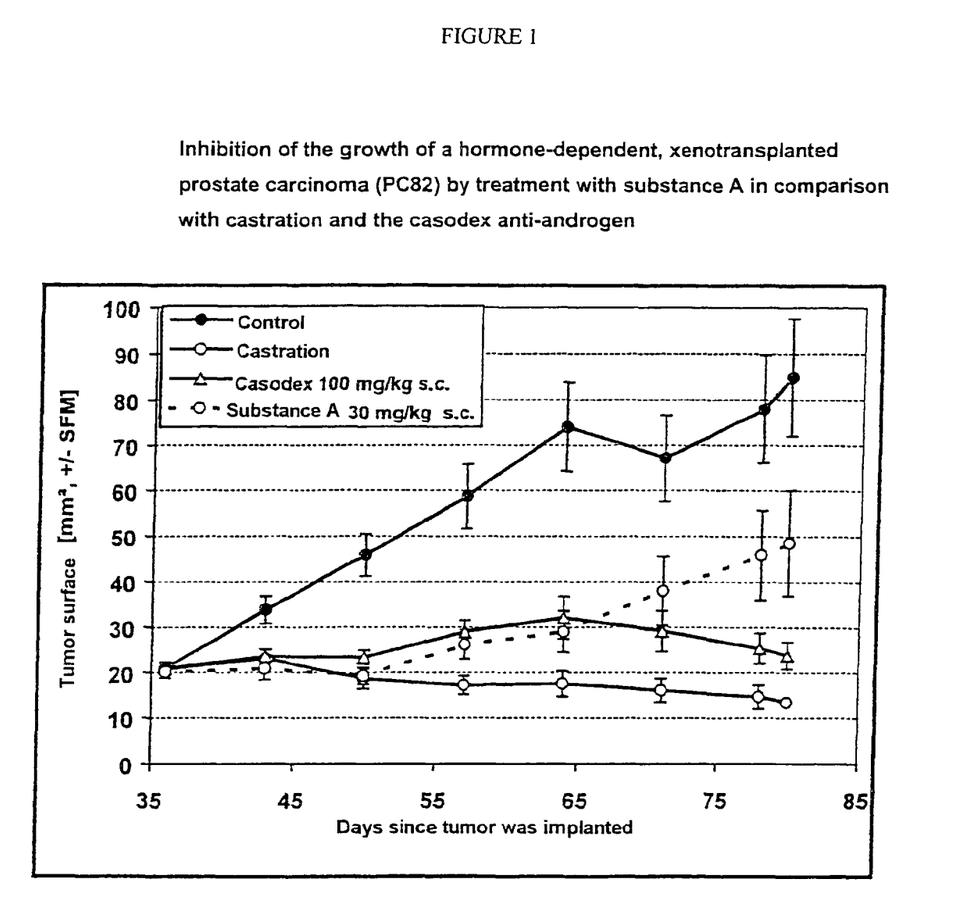
Figure 2:
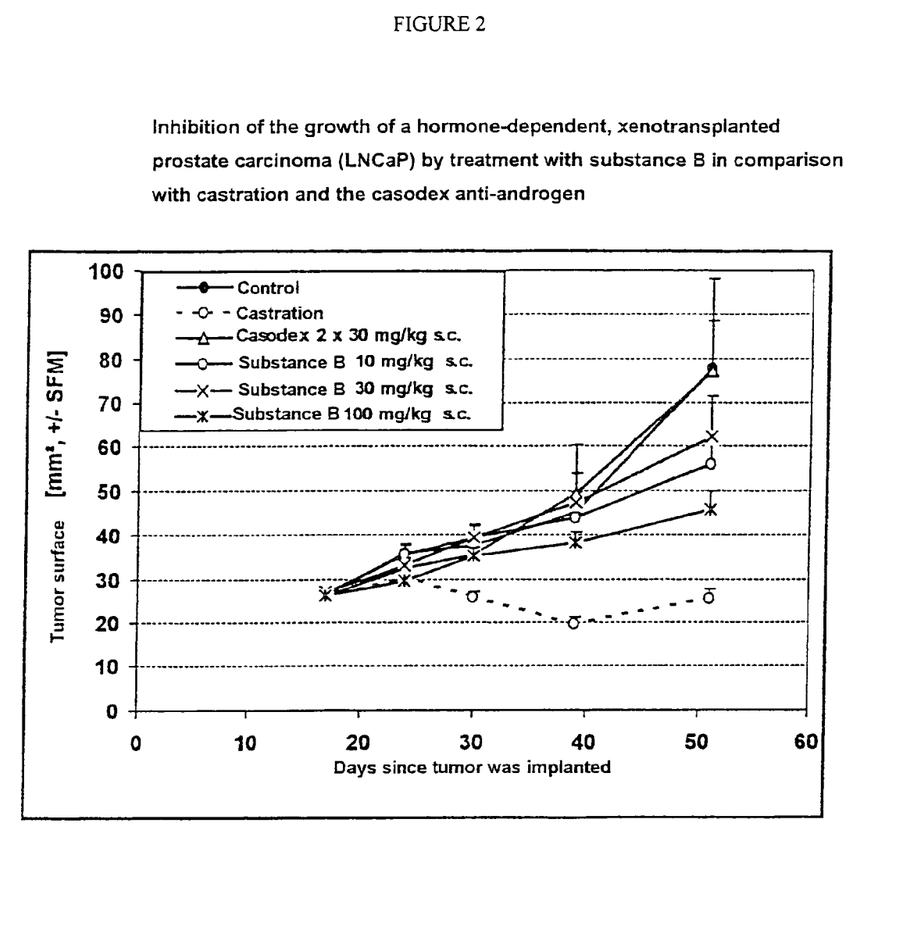

The results are shown in FIGS. 1 and 2.

While the tumor grew rapidly in untreated control animals, treatment with the inventive substances lead to a clear inhibition of the growth of the prostate tumors.

In the PC82 model, this inhibition in growth is comparable with the effects of an anti-androgen or of castration.

In the LNCaP model, a dosage-dependent inhibition of tumor growth can also be noted. Here also, the effect is comparable to castration and even superior to the treatment with casodex anti-androgen.

The results of the experiments with the prostate cancer models show that tumor growth is inhibited by the inventive substances.

In the present invention, the effect of the inventive 2-alkoxyestradiol sulfamates on tumor growth was investigated in vivo by means of a mouse xenograft model, for which the inventive compounds were administered continuously on the subcutaneous route. In comparison to the untreated control animals, tumor growth was inhibited. Retardation of tumor growth was significant in castrated mice. The treatment was tolerated well. In contrast to the castration model, shrinkage of the mouse prostate and seminal vesicle was not observed.

The present invention demonstrates that the compounds according to the invention cause an inhibition of the growth of prostate tumors.

In general, satisfactory results are to be expected when the daily doses comprise from 5 µg to 50 mg of the inventive compound per kg of body weight. For larger mammals, such as humans, the recommended daily dose ranges from 10 µg to 30 mg per kg of body weight.

Suitable dosages of the inventive compounds range from 0.005 to 50 mg per day per kg of body weight, depending on the age and constitution of the patient. The required daily dose can be administered as a single or as a multiple dose. However, because of the special sustained release effect of the estrogen sulfamates, the inventive compounds can also be administered at greater intervals than once per day (WO 00/06175).

The pharmaceutical preparations, which are based on the new compounds, are formulated in a per se known fashion by processing the active substance with vehicles, fillers, disintegration-controlling agents, binders, humectants, lubricants, absorbents, diluents, taste modifiers, coloring agents, etc., which are customary in pharmaceutical technology, and converting into the desired administration form. Reference is made to Remington's Pharmaceutical Science, 15$^{th}$ ed., Mack Publishing Company, East Pennsylvania (1980).

For oral administration, especially tablets, coated tablets, capsules, pills, powders, granulates, lozenges, suspensions, emulsions or solutions are possible. Injection and infusion preparations are possible for parenteral application. Appropriately prepared suspensions of crystals can be used for intra-articular injection. Aqueous and oily injection solutions or suspensions and appropriate sustained release preparations can be used for intramuscular injections.

For rectal administration, the new compounds can be used in the form of suppositories, capsules, solutions (for example, in the form of enemas) and ointments for systemic as well as topical therapy.

pulmonary administration, the new compounds can be used in the form of aerosols and inhalates.

For topical administration, formulations into gels, ointments, fatty ointments, creams, pastes, powders, emulsions and tinctures are possible. The dosage of the compounds of general formula I in these preparations should be 0.01% to 20%, in order to achieve an adequate pharmacological effect.

The present invention encompasses the use of the inventive compounds of general formula I for producing a medicinal drug for the treatment of tumor diseases which can be affected positively by inhibiting tubulin polymerization.

Preferably, the inventive compounds of general formula I are used to produce a medicinal drug for the treatment of tumor diseases of the male and female sexual glands and the male and female sexual organs, including the mammary glands, particularly of prostate cancer and breast cancer.

The present invention also relates to pharmaceutical compositions including at least one compound which is particularly preferred according to the invention, optionally in the form of a pharmaceutically/pharmacologically compatible salt, with no or together with pharmaceutically compatible adjuvants and/or carriers.

These pharmaceutical compositions and drugs can be provided for oral, rectal, vaginal, subcutaneous, percutaneous, intravenous or intramuscular administration. Aside from the usual carriers and/or diluents, they contain at least one compound which is particularly preferred according to the invention.

The inventive pharmaceuticals are prepared by known procedures with the usual solid or liquid carriers or diluents and commonly used pharmaceutical adjuvants in accordance with the desired type of application and with a suitable dosage. The preferred preparations consist of a form of administration, which is suitable for oral application. Such forms of administration are for example, tablets, filmcoated tablets, coated tablets, capsules, pills, powders, solutions or suspensions or also sustained release forms.

The pharmaceutical compositions, containing, at least one of the inventive compounds, preferably are administered orally.

Parenteral preparations such as injection solutions are also possible. Furthermore, for example, suppositories and means for vaginal administration may also be mentioned as preparations.

Appropriate tablets can be obtained, for example, by mixing the active substance with well-known adjuvants, e.g. inert diluents such as dextrose, sugar, sorbitol, mannitol, polyvinylpyrrolidone, disintegrants such as corn starch or alginic acid, binders such as starch or gelatin, lubricants such as magnesium stearate or talcum and/or materials for achieving a sustained release effect, such as carboxypolymethylene, carboxymethylcellulose, cellulose acetate phthalate or polyvinyl acetate. The tablets may also consist of several layers, Correspondingly, coated tablets can be prepared by coating cores, prepared in the same way as tablets, with materials conventionally used in tablet coatings, e.g. polyvinylpyrrolidone or shellac, gum arabic, talcum, titanium oxide or sugar. The coating of the tablet may also consist of several layers, where materials such as the adjuvants mentioned above for tablets are used.

Solutions or suspensions including the inventive compounds of general formula I may additionally contain taste-improving materials such as saccharin, cyclamate or sugar, as well as for example, flavors and fragrances such as vanillin or orange extract. In addition, they may contain suspending aids such as sodium carboxymethylcellulose, or preservatives such as p-hydroxybenzoates.

The capsules, containing the compounds of the general formula I, can be produced, for example, by mixing the compound(s) of general formula I with an inert carrier such as lactose or sorbitol, followed by encapsulating in gelatin capsules. Suitable suppositories can be produced, for example, by mixing with the carrier materials intended for this purpose, such as neutral fats or polyethylene glycol or derivatives thereof.

For the treatment of prostate carcinomas, the inventive compounds can be administered in combination with one or more of the following active substances:
1) antiandrogens such as CPA, flutamide, casodex, etc.
2) gonadotropic hormones (GnRH) agonists
3) 5α-reductase inhibitors such as finasteride
4) cytostatic drugs
5) VEGF kinase inhibitors
6) antigestagens
7) antiestrogens
8) antisense oligonucleotides
9) EGF antibodies
10) estrogens Moreover, the inventive compounds of general formula I can be used for the treatment and prophylaxis of other diseased states which have not been mentioned above.

The inventive compounds of general formula I can be synthesized as described below:

The electrophilic substitution of C atom 2 of an estra-1,3, 5(19)trien-17-one derivative, such as compounds 1 to 3, is preferably carried out by a Friedel-Crafts acylation, as described in the literature (T. Nambara, S. Honma, S. Akiyama, Chemical and Pharmaceutical Bulletin 1979, 18, 474-480). After changing the protective groups in position 3, a 2-carboxy-estra-1,3,5(10)-trien-17-one is produced by the Baeyer-Villiger oxidation (March, Advanced Organic Chemistry, 3$^{rd}$ Edition, J. Wiley & Sons 1985, 990-991, and references cited herein). The ester is saponified and converted into a 2-alkyl ether with an appropriate alkyl halide using a base. The protective group in position 3 is removed as described in the literature (T. W. Greene, P. G. M. Wuts, Protective Groups in Organic Synthesis, J. Wiley & Sons, 1999, pp. 249-275).

The 2-acylation, starting out from compounds of general formula II, wherein $R^2$ and $R^3$ together form a methylene bridge or which have additional double bonds in the steroid skeleton, is realized by ortho metallation (D. J. Pert, D. D. Ridley, Australian Journal of Chemistry 1989, 42, 405-419; V. Snieckus, Chemical Reviews 1990, 90, 879-933; P. Beak, R. A. Brown, Journal of Organic Chemistry, 1982, 47, 34-46).

II

Preferably, a carbamate group is used for $R^1$ as ortho-directing protective group in position 3. After lithium is introduced in the 2 position, the electrophilic substitution is performed using dimethylformamide. The 2-formylestradiol derivative is oxidized to the formic acid ester and converted by known procedures into a 2-alkoxy compound (WO 98/40398). The synthesis of compounds of general formula II, wherein $R^2$ and $R^3$ together form a methylene bridge or have the additional double bonds in the steroid skeleton, is well-known in the art (for example, DE 42 39 945; DE 42 39 946; R. Prousa, B. Schönecker, D. Tresselt, K. Ponsold, Journal für Praktische Chemie 1986, 328, 55-70; H. J. Siemann, P. Droescher, B. Undeutsch, S. Schwarz, Steroids 1995, 60, 308-315).

The present invention will be described in greater detail with reference to the following examples, without being limited thereto.

Synthesis Method

1) General Method for the Synthesis of estra-1,3,5-(10)-trien-3-yl sulfamates and estra-1,3,5(10),8-tetraen-3-yl sulfamates An estra-1,3,5(10)-trien-17-one derivative (7 mmoles) is suspended with stirring in 100 ml of methylene chloride, and 35 mmoles of 2,6-di-t-butylpyridine and 70 mmoles of sulfamoyl chloride are added at room temperature. A white to yellowish suspension is formed which is stirred for another 2 hours. The reaction mixture is added with water and extracted with ethyl acetate, and the extracts are washed with water and saturated sodium hydrogen carbonate solution until neutral. The organic phase is dried over sodium sulfate, the solvent is distilled off and the crude product is isolated. After chromatography on silica gel with a toluene/ethyl acetate eluent (v/v=1:10), the product is isolated in a yield of between 70 and 85%.

2) General Method for the Acetylation of estra-1,3,5(10)-trien-3-yl sulfamates and estra-1,3,5(10),8-tetraen-3-yl sulfamates A steroid sulfamate (10.5 mmoles), synthesized as described, is dissolved in 50 ml of pyridine and treated at a temperature of 0° to 5° C. with 115 mmoles of acetic anhydride. A clear solution is obtained, which is stirred for a further hour at room temperature. The batch is poured onto ice and extracted with ethyl acetate. After the extracts are acidified with 6N hydrochloric acid, they are washed with water and sodium chloride solution. The organic phase is dried and the solvent distilled off. The dried crude product is used without purification for further reactions.

3) General Method for Reducing 3-sulfamates and N-acetylsulfamates

The steroid (12 mmoles) is dissolved in 120 ml of a 1:1 mixture of THF and methanol and treated at room temperature portionwise with 100 mmoles of sodium borohydride. The reaction solution is stirred for 1 hour at room temperature and subsequently, after addition of water, acidified with 1M hydrochloric acid and extracted with ethyl acetate. The organic phase is washed with sodium chloride solution to neutrality and dried, and the solvent is distilled off. The crude product is purified on silica gel using toluene/ethyl acetate (v/v=3:1). The reduction product is obtained in good to very good yields (60 to 95% of theoretical).

The following inventive compounds were synthesized by the methods given:

EXAMPLE 1

2-Methoxy-17β-hydroxy-estra-1,3,5(10)-trien-3-yl sulfamate 1

1 was obtained by the general synthesis methods 1 and 3 from 13.98 mmoles of 2-methoxy-17-oxo-estra-1,3,5(10)-trien-3-ol in a yield of 10.44 mmoles (75% of theoretical).

$^1$H-NMR (400 MHz, DMSO-$d_6$, TMS) δ (ppm): 7.80 (s 2H, —NH$_2$), 6.97 (s, 1H, H-1), 6.96 (s, 1H, H-4), 4.52 (d, J=4.7 Hz, 1H, 17β-OH), 3.76 (s, 3H, 2-OCH$_3$, 3.58-3.49 (m, 1H, H-17α), 2.77-2.68 (m, 2H, H-6), 0.68 (s, 3H, H-18).

EXAMPLE 2

2-Methoxy-17β-hydroxy-14α,15α-methylene-estra-1,3,5(10)-trien-3-yl sulfamate 2

According to the general synthesis method 1 and subsequent removal of the t-butyldimethylsilyl protective group (T. W. Greene, P. G. M. Wuts, Protective Groups in Organic Synthesis, J. Wiley & Sons, 1999, pp. 273-276), 2 (1.42 mmoles, 61% of theoretical) was obtained from 2.33 mmoles of 17β-t-butyldimethylsilyloxy-2-methoxy-14α,15α-methylene-estra-1,3,5(10)-trien-3-ol.

$^1$H-NMR (400 MHz, DMSO-$d_6$, TMS) δ (ppm): 7.80 (s, 2H, —NH$_2$), 6.95 (s, 1H, H-1), 6.94 (s, 1H, H-4), 5.67 (s, 1H, 17β-OH), 3.74 (s, 3H, 2-OCH$_3$), 3.56-3.50 (m, 1H, H-17α), 2.80-2.62 (m, 2H, H-6), 0.89 (s, 3H, H-18), 0.28-0.20 (m, 2H, 14α,15α-CH$_2$).

EXAMPLE 3

2-Ethoxy-17β-hydroxy-estra-1,3,5(10)-trien-3-yl sulfamate 3

3 was obtained in a yield of 1.23 mmoles (75% of theoretical) from 1.64 mmoles of 2-ethoxy-17-oxo-estra-1,3,5(10)-trien-3-ol by the general synthesis methods 1 and 3.

$^1$H-NMR (400 MHz, DMSO-$d_6$, TMS) δ (ppm): 7.76 (s, 2H, —NH$_2$), 6.96 (s, 1H, H-1), 6.95 (s, 1H, H-4), 4.53 (d J=3.9 Hz, 1H 17β-OH), 4.07-3.99 (m, 2H, 2-OCH$_2$CH$_3$), 3.59-3.48 (m, 1H H-17α), 2.76-2.69 (m, 2H, H-6), 1.31 (t, J=7.0 Hz, 3H 2-OCH$_2$CH$_3$), 0.71 (s, 3H, H-18).

EXAMPLE 4

2-Methoxy-17β-hydroxy-estra-1,3,5(10)-trien-3-yl N-acetylsulfamate 4

6 was obtained in a yield of 1.05 mmoles (73% of theoretical) from 1.43 mmoles of 2-methoxy-17-oxo-estra-1,3,5(10)-trien-3-ol by the general synthesis methods 1, 2 and 3.

¹H-NMR (400 MHz, DMSO-d₆, TMS) δ (ppm): 12.20 (s, 1H, —NH), 6.97 (s, 1H, H-1), 6.92 (s, 1H, H-4), 4.51 (d, J=3.5 Hz, 1H, 17β-OH), 3.73 (s, 3H, 2-OCH₃), 3.57-3.48 (m, 1H, H-17α), 2.75-2.67 (m, 2H, H-6) 1.99 (s, 3H, —NCOCH₃), 0.68 (s, 3H, H-18).

EXAMPLE 5

2-Methoxy-17β-hydroxy-14α,15α-methylene-estra-1,3,5(10)-trien-3-yl N-acetylsulfamate 5

7 was obtained in a yield of 1.19 mmoles (51% of theoretical) from 2.33 mmoles of 17β-t-butyldimethylsilyloxy-2-methoxy-14α,15α-methylene-estra-1,3,5(10)-trien-3-ol by the general synthesis methods 1 and 2 and subsequent removal of the t-butyldimethylsilyl protective group (T. W. Greene, P. G. M. Wuts, Protective Groups in Organic Synthesis, J. Wiley & Sons, 1999, pp. 273-276).

¹H-NMR (400 MHz, DMSO-d₆, TMS) δ (ppm): 12.20 (s, 1H, —NH), 6.95 (s, 1H, H-1), 6.92 (s, 1H, H-4), 5.67 (s, 1H, 17β-OH), 3.74 (s, 3H, 2-OCH₃), 3.56-3.50 (m, 1H, H-17α), 2.80-2.62 (m, 2H, H-6), 1.97 (s, 3H, —NCOCH₃), 0.89 (s, 1H, H-18), 0.28-0.20 (m, 2H, 14α,15α-CH₂).

EXAMPLE 6

2-Ethoxy-17β-hydroxy-estra-1,3,5(10)-trien-3-yl N-acetylsulfamate 6

8 was obtained in a yield of 0.94 mmoles (67% of theoretical) from 1.40 mmoles of 2-ethoxy-17-oxo-estra-1,3,5(10)-trien-3-ol using the general synthesis methods 1, 2 and 3.

¹H-NMR (400 MHz, DMSO-d₆, TMS) δ (ppm): 12.20 (s, 1H, —NH), 6.99 (s, H-1), 6.86 (s, 1H, H-4), 4.53 (d, J=4.7 Hz, 1H, 17β-OH) 4.07-3.96 (m, 3H, 2-OCH₂CH₃), 3.56-3.50 (m, 1H, H-17α), 2.74-2.68 (m, 2H, H-6), 1.97 (s, 3H, —NCOCH₃), 1.29 (t, 3H, 2-OCH₂CH₃), 0.68 (s, 3H, H-18).

EXAMPLE 7

2-Methoxy-17α-hydroxy-14α,15α-methylene-estra-1,3,5(10),8-tetraen-3-yl sulfamate 7

11 was obtained in a yield of 1.08 mmoles (65% of theoretical) from 1.67 mmoles of 17α-t-butyldimethylsilyloxy-2-methoxy-14α,15α-methylene-estra-1,3,5(10),8-tetraen-3-ol using the general synthesis method 1 and subsequent removal of the t-butyldimethylsilyl protective group (T. W. Greene, P. G. M. Wuts, Protective Groups in Organic Synthesis, J. Wiley & Sons, 1999, pp. 273-276).

¹H-NMR (400 MHz, DMSO-d₆, TMS) δ (ppm): 7.81 (s, 2H, —NH₂), 6.98 (s, 1H, H-1), 6.93 (s, 1H, H-4), 3.90 (d, J=6.2 Hz, 1H, H-17β), 3.80 (s, 3H, 2-OCH₃) 2.80-2.62 (m, 2H, H-6), 1.28-1.25 (m, 1H, 14α,15α-CH₂), 0.93 (s, 1H, H-18), 0.47-0.43 (m, 1H, 14α,15α-CH₂).

EXAMPLE 8

2-Methoxy-17α-hydroxy-14α,15α-methylene-estra-1,3,5(10),8-tetraen-3-yl N-acetylsulfamate 8

12 was obtained in a yield of 0.91 mmoles (48% of theoretical) from 1.89 mmoles of 17α-t-butyldimethylsilyloxy-2-methoxy-14α,15α-methylene-estra-1,3,5(10),8-tetraen-3-ol by the general synthesis methods 1 and 2 and subsequent removal of the t-butyldimethylsilyl protective groups (T. W. Greene, P. G. M. Wuts, Protective Groups in Organic Synthesis, J. Wiley & Sons, 1999, pp. 273-276).

¹H-NMR (400 MHz, DMSO-d₆, TMS) δ (ppm): 12.20 (s, 1H, —NH), 6.98 (s, 1H, H-1), 6.90 (s, 1H, H-4), 3.89 (d, J=6.1 Hz, 1H, H-17(3), 3.80 (s, 3H, 2-OCH₃), 2.80-2.62 (m, 2H, H-6), 1.96 (s, 3H, —NCOCH₃), 1.28-1.25 (m, 1H, 14α,15α-CH₂), 0.93 (s, 1H, H-18), 0.47-0.40 (m, 1H, 14α,15α-CH₂).

The invention claimed is:

1. A compound of formula I, wherein
R¹ is C₁-C₄ acyl,
R² is H, methyl, C₁-C₄ acyl, or benzoyl,
R³ is C₁-C₄ alkyl or a group of formula $C_nF_mH_o$,
n is 1, 2, 3, 4, 5 or 6,
m is >1,
m+o is 2n+1,
R⁴ and R⁵ are both H, or together are a methylene or an additional double bond,
R⁶ is H, and
R⁷ is OC₁-C₁₁-acyl or OSO₂NR¹R²,
wherein the dashed lines in formula I represent up to two double bonds.

2. A compound according to claim 1, wherein R³ is methyl, ethyl or 2,2,2-trifluoroethyl.

3. A compound according to claim 1, wherein R² is H.

4. A compound according to claim 1, wherein R³ is a methyl group.

5. A pharmaceutical composition comprising a compound of claim 1 and a pharmaceutically acceptable adjuvant and/or carrier.

6. A pharmaceutical composition comprising a compound of claim 2 and a pharmaceutically acceptable adjuvant and/or carrier.

7. A method for inhibiting tubulin polymerization comprising administering an effective amount of a compound according to claim 1 to a subject, thereby inhibiting tubulin polymerization in the subject.

8. A method for inhibiting tubulin polymerization comprising administering an effective amount of a compound according to claim 2 to a subject, thereby inhibiting tubulin polymerization in the subject.

9. A method for inhibiting tubulin polymerization comprising administering an effective amount of a compound according to claim 1 to a subject, thereby inhibiting tubulin polymerization in the subject, wherein the subject has prostate cancer.

10. A method of inhibiting tubulin polymerization comprising administering an effective amount of a compound according to claim 1 to a subject, thereby inhibiting tubulin polymerization in the subject, wherein said subject has breast cancer.

11. A method for inhibiting tubulin polymerization comprising administering an effective amount of a compound according to claim 2 to a subject, thereby inhibiting tubulin polymerization in the subject, wherein the subject has prostate cancer.

12. A method for inhibiting tubulin polymerization comprising administering an effective amount of a compound according to claim 2 to a subject, thereby inhibiting tubulin polymerization in the subject, wherein the subject has breast cancer.

13. A compound according to claim 1, wherein $R^4$ and $R^5$ are both H.

14. A compound according to claim 1, wherein $R^4$ and $R^5$ together are a methylene.

15. A compound according to claim 1, wherein $R^4$ and $R^5$ are an additional double bond.

16. A compound according to claim 1, wherein $R^7$ is $OC_1$-$C_{11}$-acyl.

17. A compound according to claim 1, wherein $R^7$ is $OSO_2NR^1R^2$.

18. A compound according to claim 1, wherein $R^2$ is methyl.

19. A compound according to claim 1, wherein $R^2$ is $C_1$-$C_4$ acyl.

20. A compound according to claim 1, wherein $R^2$ is benzoyl.

21. A compound according to claim 1, wherein $R^3$ is a group of formula $C_nF_mH_o$.

* * * * *